United States Patent [19]

Buckles et al.

[11] 4,201,207
[45] * May 6, 1980

[54] BLADDER FOR LIQUID DISPENSER

[75] Inventors: Richard G. Buckles, Redwood City; Harold M. Leeper, Mountain View, both of Calif.

[73] Assignee: ALZA Corporation, Palo Alto, Calif.

[*] Notice: The portion of the term of this patent subsequent to Nov. 23, 1993, has been disclaimed.

[21] Appl. No.: 745,132

[22] Filed: Nov. 26, 1976

Related U.S. Application Data

[63] Continuation-in-part of Ser. No. 598,490, Jul. 23, 1975, abandoned, which is a continuation-in-part of Ser. No. 344,861, Mar. 26, 1973, abandoned.

[51] Int. Cl.² .................. A61M 5/00; B65D 35/18; C08C 19/00; C08C 19/04
[52] U.S. Cl. .................. 128/214 F; 128/DIG. 12; 222/206; 222/215; 525/334; 525/387
[58] Field of Search .............. 526/57, 21; 128/214 F, 128/DIG. 12; 222/215, 206

[56] References Cited

U.S. PATENT DOCUMENTS

| | | | |
|---|---|---|---|
| 2,816,690 | 12/1957 | Lari | 222/92 |
| 2,819,255 | 1/1958 | Boardman | 260/94.7 |
| 3,129,204 | 4/1964 | Gilmont | 260/94.7 |
| 3,339,809 | 12/1967 | Church et al. | 222/215 |
| 3,486,539 | 12/1969 | Jacuzzi | 128/DIG. 12 |
| 3,791,557 | 2/1974 | Venus | 222/386.5 |
| 3,993,069 | 11/1976 | Buckles et al. | 128/214 F |

OTHER PUBLICATIONS

Vulcanization of Polymers (L. O. Amberg), pp. 286–287, Edited by Alliger et al., Reinhart Corp. 1964.

Primary Examiner—William F. Hamrock
Attorney, Agent, or Firm—Thomas E. Ciotti; Paul L. Sabatine; Edward L. Mandell

[57] ABSTRACT

An improvement in liquid dispensers, especially those used to infuse liquid drugs into patients, that dispense liquid under pressure from an expansible, elastomer bladder is disclosed. The improvement is that the bladder is made from synthetic vulcanized polyisoprene, especially polyisoprene that has 90% to 98% cis linkages and has been vulcanized with an organic peroxide, such as dicumyl peroxide, at a concentration of $5.5 \times 10^{-3}$ to $7.5 \times 10^{-3}$ moles of peroxide per 100 grams of polyisoprene.

17 Claims, 3 Drawing Figures

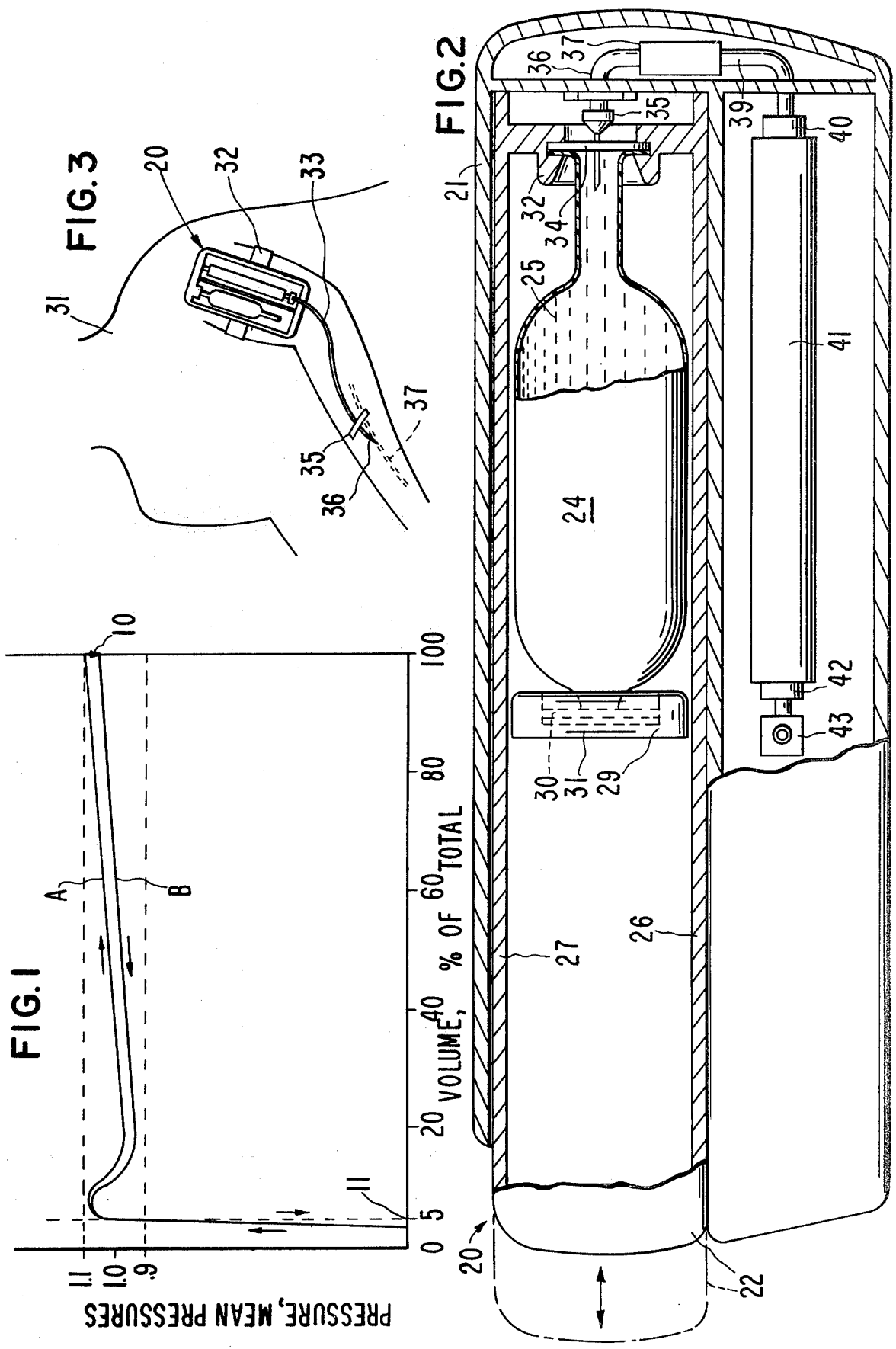

BLADDER FOR LIQUID DISPENSER

CROSS REFERENCE TO RELATED APPLICATIONS

This application is a continuation-in-part of application Ser. No. 598,490 filed July 23, 1975 which in turn is a continuation-in-part of application Ser. No. 344,861, filed Mar. 26, 1973 and now abandoned.

BACKGROUND OF THE INVENTION

1. Field of the Invention

This invention relates to an improvement in liquid dispensers that dispense liquid under pressure from an elastomeric bladder.

2. Description of the Prior Art

It is well known that when a fluid is pressured into an elastic container so as to distend the container walls, these elastic walls apply pressure to the liquid. This pressure may be used to propel the liquid out of the container. This relationship finds embodiment in such items as water balloons, pressure accumulators, sprayers, pressure pack barrels and intravenous infusion devices. See for instance the references cited in the file of the above mentioned parent application Ser. No. 344,861. All of these fluid dispensers share the same basic structure. Each has a distensible elastic bag or bladder that applies pressure to an enclosed liquid and forces the liquid through a valve that modulates the rate of flow of liquid from the bladder.

The bladders employed in the prior art are variously described as constructed of natural rubber or of other suitable elastomeric materials. While elastomers generally may be used in such bladders, as a general class they fail to provide a constant pressure on the fluid as the fluid is discharged. Instead, they permit the pressure to decrease significantly as liquid is pumped out. This inability to provide a constant pressure is especially disadvantageous in situations in which a constant flow rate is desired. Only with complicated, continually-changing variable flow valves is it possible to maintain a constant flow as the pressure decreases.

SUMMARY OF THE INVENTION

The invention is an improvement in liquid dispensers that dispense liquid from an expansible, elastomeric bladder. Such dispensers comprise in combination: an expansible elastic bladder that holds the liquid under pressure, the elastic force in whose walls provides the force by which the liquid is dispensed; a flow passage communicating with the interior of the bladder and extending to the exterior thereof; and a flow control element in the flow passage that regulates the rate of flow of liquid through the passage. The improvement is that the bladder is made of synthetic, vulcanized polyisoprene.

In many embodiments the dispenser includes a housing in which the bladder is contained. In such embodiments the invention includes the further improvement that the bladder is contained in the housing in a manner in which it is substantially unrestricted in its deflated and inflated states.

As compared to the prior art dispensers in general, the improved dispensers of the invention dispense liquid at a more nearly constant pressure. And, as compared to prior art dispensers that employ natural rubber bladders—which the art generally recognizes as being the best kind of bladder—the dispensers of the invention exhibit less stress decay and less low frequency hysteresis. These features are manifested in the following performance characteristics which distinguish the hereinafter described preferred embodiment of the invention:

(1) The pressure on the liquid remains constant (within ±10% of mean pressure) during the discharge of up to about 90% of the bladder contents, even when the discharge is at a very slow rate, say 0.1–1.0 ml/hr.

(2) The discharge includes at least 95% of the initial contents.

(3) The discharge retains these desirable characteristics (1 and 2 above) even when the discharge is prolonged or delayed over substantial periods of time.

BRIEF DESCRIPTION OF THE DRAWINGS

In the accompanying drawings:

FIG. 1 is a graph illustrating a pressure/volume curve of a polyisoprene bladder in accord with the present invention;

FIG. 2 is a partial, cross-sectional, top view of a dispenser of this invention adapted for infusing drugs into a patient; and FIG. 3 is a perspective, elevational view showing the dispenser of FIG. 2 being used.

DETAILED DESCRIPTION OF THE INVENTION

The bladder of the improved dispensers of the invention is fabricated from vulcanized synthetic polyisoprene. The polyisoprene has a significant proportion, but not all, of its monomeric units joined with a cis orientation. More specifically, it is preferred if from about 85% to about 98% of the monomeric units have cis bonding. If more than 98% of the bonds are of a cis orientation, the resulting polymer will be too crystalline and not have the desired elastomeric properties. If less than 85% of the bonds are cis, the elastomeric properties may suffer as well. The most preferred polyisoprenes have about 90% to about 98% cis orientation. Minor amounts of appropriate rubbers, such as butadiene rubber and natural rubber, may be blended with the polyisoprene if desired. Additives such as filler, reinforcing agents, antioxidants, pigments, and the like may also be formulated with the polyisoprene. However, care must be used in such formulation in order to avoid deleteriously affecting the performance of the bladder.

The above described polyisoprenes are vulcanized to form carbon-to-carbon or monothio cross-links in the polymer network. After vulcanization, the polyisoprene is characterized by extremely low decay of stress when stretched to constant extension, very low hysteresis on extension and contraction, and very low permanent set. The cross-link density of the vulcanized polymer will usually be about 16 to about 24 cross-links per polyisoprene molecule (M/Mc in the Flory-Rehner equation). Organic peroxides may be used as vulcanizing agents to form the carbon-to-carbon cross-linked variety of polyisoprene and thiuram disulfides may be used to form the monothio cross-linked variety. Organic peroxides are preferred vulcanizing agents and the carbon-to-carbon cross-linked polyisoprene is correspondingly preferred. The quantity of vulcanizing agent significantly affects the relevant mechanical properties of the vulcanisate. Too much agent will result in a brittleness; whereas too little will result in poor hysteresis, stress decay, and permanent set. In the case at hand, concentrations of about $5.5 \times 10^{-3}$ to about $7.5 \times 10^{-3}$ moles of active peroxide per 100 g of polyisoprene have been found to be useful, with about $6.7 \times 10^{-3}$ moles of active peroxide per 100 g of polyisoprene being preferred.

Peroxides that may be used as vulcanizing agents in the invention include benzoyl peroxide, 1,1-di-t-butyl-peroxy-3,3,5-trimethylcylohexane, n-butyl-4,4-bis(t-butylperoxy)valerate, $\alpha,\alpha'$-bis(t-butylperoxy)diisopropylbenzene, di-t-butyl peroxide, and dicumyl peroxide. Dicumyl peroxide is preferred. Sulfides that may be used as vulcanizing agents include tetramethyl thiuram disulfide, tetraethyl thiuram disulfide and 4,4'-dithiomorpholine. Tetramethyl thiuram disulfide is preferred.

The above described polyisoprenes have a stress relaxation of less than about 10% and a low frequency hysteresis of less than about 10%. Stress relaxation is measured by preparing samples of the polyisoprene according to ASTM 412-68 (Die C), elongating the samples to 300% to 2.0 in/min on an Instron tensile tester, maintaining the samples at that elongation for approximately one day, and retracting the samples at the same speed as used for elongating them. Stress relaxation is calculated by dividing the difference between (1) the stress immediately after elongation and (2) the stress immediately before retraction by (1). Low frequency hysteresis is measured in the same manner as stress relaxation except that the samples are retracted immediately after elongation. Hysteresis is expressed as the percent difference between the integral of the stress/strain curve for elongation and the integral of the stress/strain curve for retraction.

It is also preferred that polyisoprene bladders of this invention meet the following geometrical criteria: that they be generally cylindrical, that the deflated length of the bladder be 5 or more times its deflated outside diameter, usually 5–20, and that the walls of the bladder be in thickness from 0.01 to 1, usually 0.1 to 0.5, times the deflated inside diameter. With such geometry, the bladders of the invention provide an especially good liquid discharge, namely one wherein the pressure on the liquid throughout the delivery varies from the mean pressure (herein defined as $P_{(m)}$) and $$P_{(m)} = \frac{1}{V_{TOT}} \cdot \int_0^{V_{TOT}} P dV$$

wherein $P_{(m)}$=mean pressure, P=pressure, V=volume and $V_{TOT}$=the total volume delivered) by not more than $\pm 10\%$ over discharge of up to about 90% of the bladder's contents. Also, with this geometry, the residual volume (dead volume) is less than 5% of the inflated capacity, that is:

$$\frac{\text{Capacity} - V_{TOT}}{\text{Capacity}} \cdot 100 \leq 5\%.$$

The very low residual volume means that the amount of liquid lost in the dead volume and hence undelivered, is likewise low.

The liquid discharge characteristics of the improved bladders of the invention are shown in FIG. 1, a pressure/volume curve of a vulcanized, synthetic polyisoprene bladder having the preferred geometry described above. Curve A is the inflation curve as liquid is pressured into the bladder and Curve B is the deflation curve as liquid is slowly pumped out. The elastic force in the wall of the bladder provides the sole force by which the liquid is pumped out of the bladder. Several parts of Curve B merit mention. As can be seen, the pressure on the enclosed liquid remains essentially constant throughout the major portion of the deflation curve. Also, it will be noted, at point 10 on the curve, that the loss of pressure prior to deflation due to stress relaxation is very small and, at point 11 on the curve, that the residual volume (volume not pumped out) is small, in fact, less than 5% of the filled volume.

The bladders of the present invention are used to store and dispense fluids, including pure liquids, solutions, gels, suspensions and the like at a constant pressure optionally over a prolonged period of time. Such bladders thus find application in a wide range of uses, for example, dispensing medical fluids, biological agents and nutritional fluids, to name but a few.

A preferred embodiment of the dispensers of this invention is an apparatus for infusing drugs into the bodies of humans or other living creatures. (As used herein, "drugs" includes all manner of medicaments and liquid drug formulations.) In such apparatuses, in combination with means for restricting flows of liquid to a very low rate, the polyisoprene bladders make possible compact units for infusing drugs to bodies under pressure at constant rates. Drug infusion devices employing this invention have numerous advantages over conventional infusion devices. First, they overcome the use of cumbersome gravity-fed intravenous "drip" systems. Second, by their small size and positional insensitivity (since they operate independently of gravity) they may be fastened to the user and permit the user to be ambulatory. Third, the devices offer the advantage of being able to administer very small flows of drug, such as 0.1 to 1 ml of drug/hr. The prior art "drip" systems were most difficult to calibrate or control at rates much lower than about 10 ml/hr. This decrease in volume of delivered fluid is of benefit in many medical conditions, such as in heart disease, where it is undesirable to increase circulatory system volume even by a small amount.

A very simple device can employ the present invention for drug infusion purposes. All that is needed is a polyisoprene bladder of this invention filled with liquid, a flow control, means to conduct the controlled flow of drug and a suitable needle or catheter to pass the controlled flow of drug to the infusion site on the patient. The needle or catheter is inserted into an artery or vein and the drug infused thereinto. The delivery device is, if desired, affixed to the patient by, for example, straps, tape or the like, thus permitting the patient to be ambulatory.

A more sophisticated drug infusion device embodying the improvement of this invention is depicted as device 20 in FIG. 2. Device 20 comprises a structural base 21 in which the elements of the drug infusion device are mounted. In practice, base 21 is made up of one or several plastic castings and presents a closed smooth surface enclosing the elements. Here, for purposes of illustration, it is shown cut away. Auxiliary base 22 slidably engages base 21 and is held in the relation shown by latches or similar fastening means. Located within auxiliary base 22 is elastomeric bladder 24, comprised of a polymer of this invention and dimensioned as is preferred in accord with this invention. Bladder 24 is filled with and distended (inflated) by liquid medicament 25. Walls 26 and 27 of auxiliary base 22 enclose bladder 24 but are positioned so as not to significantly touch or restrict bladder 24 in either inflated or deflated form. One end of bladder 24 is affixed to slide 29 via fastening seal 30. Slide 29 functions to smooth the contraction of bladder 24 and to indicate by mark 31 and a scale (not shown) in auxiliary base 22 the extent of expansion of bladder 24, and hence how much drug it contains. Slide 29 and seal 30 may, if desired, be adapted with the addition of septums, valves and the like to permit the charging of liquid drug into bladder 24, or the bleeding of gas (air) from the bladder. The end of bladder 24 distal from slide 29 fixedly engages auxiliary base 22 via clamp ring 32. This end of bladder 24 is equipped with connecting means through which connection can be made between liquid medicament 25 and the device. In FIG. 2 this connecting means comprises a penetrable septum sealing the end of bladder 24, which septum may be penetrated by hollow needle 35. Alternative arrangements, such as a position-controlled valve or the like could also be suitably employed. When bladder 24 is connected via septum 34 and needle 35, liquid medicament is forced via the elastic pressure of bladder 24 through needle 35 to conduit 36, filter 37, conduit 39 and connector 40 to flow control 41. Filter 37 is an optional component. It is useful to prevent microbial contamination. Flow control 41 comprises means for regulating the flow of fluid therethrough to low rates such as 0.1 ml/hr to about 10 ml/hr. The controlled flow of drug passes through connecter 42 and through fitting 43. A suitable catheter assembly (not shown) is attached to fitting 43 to conduct drug to the patient. The rate of flow of drug is restricted by flow control 41. The actual embodiment of flow control 41 is not critical to the practice of this invention and encompasses all functional equivalents.

While higher and lower flow rates and pressures may be employed, bladder 24 and flow control 41 are generally designed to permit the delivery of from 0.1 to 50 ml/hr of drug at pressures of from 2 psi to 100 psi. The volume of drug 25 in bladder 24 may range from about 5 ml to about 75 ml. Generally, for a portable drug delivery unit the volume of drug 25 is from 10 ml to 40 ml.

Turning to FIG. 3, a human torso 15 is illustrated having delivery device 20, as set forth in FIG. 2, attached to its left arm by strap or tape 16. Tube 23 leads from device 20 and conducts drug therefrom to vein or artery 19 via needle 18. Element 17 is a tape holding tube 33 and needle 18 in place.

The following examples set forth illustrative embodiments of the invention. These embodiments are not to be construed as limiting the scope of this invention.

EXAMPLE 1

A 1000 gram portion of solid Ameripol SN 600 brand polyisoprene, having a 92-98% cis content, is placed in a mill and masticated at 120° F., 18 grams of dicumyl peroxide are thoroughly blended through the polyisoprene and the mixture is extruded as a 1/10 in. thick sheet. Two pieces of this sheet are laid in a compression mold which has four cavities, each shaped to give a hollow cylindrical bladder having an inside diameter of ⅛ in., an outside diameter of 3/16 in., a wall thickness of 1/32 in. and a length of 3 in. Such a bladder meets the geometrical limitations preferred with the present invention, having a wall thickness equal to 0.25 times the inside diameter and a length which is 24 times the inside diameter. The mold is compressed about the two pieces of rubber sheet and held under pressure at 330° F. for 20 minutes. During this period the polyisoprene is formed to the shape of the mold and the polyisoprene is crosslinked by the peroxide. The mold is opened and the polyisoprene tubes are removed.

One of the resulting bladders is attached to a water supply and a metering valve filled with 30 ml of water and the valve then closed. There is a pressure gauge attached to the bladder, upstream of the metering valve. The inflated bladder is a cylindrical "sausage". The pressure inside the bladder is 600 mm of mercury. The valve is opened to permit a flow of about 1 to 1.1 ml/hr of water from the bladder. The pressure is monitored as the bladder deflates and is found to vary between 600 and 565 mm during deflation from 30 ml to 2 ml (less than a ±10% variation from the mean). Below 2 ml it drops rapidly. The total volume of liquid expelled is 29 ml, or 97% of the original.

EXAMPLE 2

A 1000 gram portion of solid Ameripol SN 600 brand polyisoprene, having a 92-98% cis content, is placed on a rubber mill and masticated at 150° F., 18 grams of dicumyl peroxide ($6.67 \times 10^{-3}$ moles of peroxide per 100 grams polyisoprene) are thoroughly blended through the polyisoprene and the mixture is sheeted as a 0.1 in. thick sheet. A 10 gram portion of the mixture was inserted into a six cavity transfer mold to form cylindrical bladders having an inside diameter of 0.124 in., an outside diameter of 0.174 in., and a length of about 1.6 in. Such a bladder meets the geometrical limitations preferred with the present invention, having a wall thickness equal to 0.20 times the inside diameter and a length which is 12-13 times the inside diameter. The rubber is cured under pressure at 330° F. for 20 minutes.

One of the resulting bladders is attached to a water supply and a metering valve filled with 25 ml of water and the valve then closed. There is a pressure gauge attached to the bladder, upstream of the metering valve. The inflated bladder is a cylindrical "sausage". The pressure inside the bladder is 10.7 psi. The valve is opened to permit a flow of about 10 ml/hr of water from the bladder. The pressure is monitored as the bladder deflates and is found to vary between 11.6 and 10.1 psi during deflation from 25 ml to 2 ml (less than a ±10% variation from the mean). The total volume of liquid expelled is 24.5 ml, or 98% of the original.

EXAMPLE 3

The experiment of Example 2 is repeated substituting 46 grams of Percadox 17/40 brand of n-butyl-4,4-bis(t-butylperoxy)valerate for the dicumyl peroxide. The resulting reservoir had a static pressure of 10.3 psi. During deflation from 25 ml to 3 ml the pressure varied from 11.3 to 9.4 psi. The total volume expelled was 24.5 ml or 98% of the original volume.

EXAMPLES 4 & 5

The experiment of Example 2 is repeated with polyisoprene having varying levels of dicumyl peroxide. The results of these experiments are reported below:

| Moles of Peroxide per 100 g of Polyisoprene | Static Pressure, psi |
|---|---|
| $5.9 \times 10^{-3}$ | 9.1 |
| $7.4 \times 10^{-3}$ | 12.0 |

In all cases better than 95% of the bladder contents were delivered.

EXAMPLE 6

The experiment of Example 1 is repeated using a polyisoprene compostion of the following formula, cured for 20 min. at 310° F.:

| phr | Ingredient | Grams |
|---|---|---|
| 100 | Ameripol SN 600 polyisoprene | 50 |
| 3 | Stearic Acid | 1.5 |
| 4 | Zinc Oxide | 2 |
| 4 | Tetramethyl thiuram disulfide (TMTD) | 2 |

The resulting bladder is inflated with 25 ml liquid giving a static pressure of 10.35 psi. The pressure varies from 10.7 to 9.3 psi during the deflation from 25 ml to 3 ml.

Modifications of the above described invention that are obvious to those of skill in the relevant arts are intended to be within the scope of the following claims.

We claim:

1. In a dispenser for dispensing a liquid under pressure comprising an expansible elastic bladder for holding the liquid under pressure, the elastic force in whose walls provides the force by which the liquid is dispensed, a flow passage from the bladder, and flow metering means in the flow passage, the improvement wherein the bladder is made of vulcanized, synthetic polyisoprene having a stress relaxation of less than about 10% and a low frequency hysteresis of less than about 10%.

2. The improvement of claim 1 wherein the polyisoprene has from about 85% to about 89% cis linkages.

3. The improvement of claim 1 wherein the polyisoprene has from about 90% to about 98% cis linkages.

4. The improvement of claim 3 wherein the vulcanization has formed cross-links in the polyisoprene, the density of which is about 16 to about 24 cross-links per polyisoprene molecule.

5. The improvement of claim 3 wherein the polyisoprene has been vulcanized with an organic peroxide at a concentration of about $5.5 \times 10^{-3}$ to about $7.5 \times 10^{-3}$ moles of peroxide per 100 grams of polyisoprene.

6. The improvement of claim 5 wherein the peroxide is a dicumyl peroxide.

7. The improvement of claim 3 wherein the polyisoprene has been vulcanized with dicumyl peroxide at a concentration of about $6.7 \times 10^{-3}$ moles of peroxide per 100 grams of polyisoprene.

8. The improvement of claim 1 wherein the dispenser includes a housing and the bladder is contained in the housing in a manner in which it is substantially unrestricted in its deflated and inflated states.

9. In an apparatus for infusing liquid drug into a patient at a controlled rate and under an essentially constant pressure comprising: an elastomeric, expansible, generally cylindrical bladder for holding the liquid, said bladder having a deflated length that is not less than 5 times the deflated outside diameter and a wall thickness of from 0.01 to 1 times the deflated inside diameter, the elastic force in the wall of the bladder providing said pressure; a flow passage that communicates with the interior of the bladder and extends to the infusion site; and a flow control element in the passage for regulating the flow of liquid through the passage, the improvement wherein the bladder is made from synthetic, vulcanized polyisoprene having a stress relaxation of less than about 10% and a low frequency hysteresis of less than about 10%.

10. The improvement of claim 9 wherein the polyisoprene has about 85% to about 98% cis linkages.

11. The improvement of claim 9 wherein the polyisoprene has from about 90% to about 98% cis linkages.

12. The improvement of claim 11 wherein the vulcanization has formed cross-links in the polyisoprene, the density of which is about 16 to about 24 cross-links per polyisoprene molecule.

13. The improvement of claim 11 wherein the polyisoprene has been vulcanized with an organic peroxide at a concentration of about $5.5 \times 10^{-3}$ to about $7.5 \times 10^{-3}$ moles of peroxide per 100 grams of polyisoprene.

14. The improvement of claim 13 wherein the peroxide is dicumyl peroxide.

15. The improvement of claim 11 wherein the polyisoprene has been vulcanized with dicumyl peroxide at a concentration of about $6.7 \times 10^{-3}$ moles of peroxide per 100 grams of polyisoprene.

16. The improvement of claim 9 wherein the apparatus includes a housing that contains the bladder, and the bladder is contained in the housing in a manner in which it is unrestricted in its inflated and deflated states.

17. The improvement of claim 9 wherein the bladder has a deflated length that is 5 to 20 times its deflated inside diameter and a wall thickness of from 0.1 to 0.5 times its deflated inside diameter.

* * * * *